United States Patent [19]

Benson

[11] 4,022,215
[45] May 10, 1977

[54] CRYOSURGICAL SYSTEM

[76] Inventor: Jerrel W. Benson, 2580 Snowberry Lane, Pepper Pike, Ohio 44124

[22] Filed: Dec. 10, 1973

[21] Appl. No.: 423,013

[52] U.S. Cl. .................................. 128/303.1
[51] Int. Cl.² ................................. A61B 17/36
[58] Field of Search ................ 62/293; 128/303.1

[56] References Cited

UNITED STATES PATENTS

| | | | |
|---|---|---|---|
| 2,305,367 | 12/1942 | Webb | 62/293 |
| 3,369,550 | 2/1968 | Armao | 128/303.1 |
| 3,421,508 | 1/1969 | Nestrock | 62/293 X |
| 3,439,681 | 4/1969 | Riley | 128/402 X |
| 3,467,104 | 9/1969 | Burbridge et al. | 128/402 X |
| 3,534,739 | 10/1970 | Bryne | 128/303.1 |
| 3,536,075 | 10/1970 | Thomas, Jr. | 128/303.1 |
| 3,786,814 | 1/1974 | Armao | 128/303.1 |
| 3,900,035 | 8/1975 | Welch et al. | 128/402 |

OTHER PUBLICATIONS

Zacarian, S.A., "Cryosurgery in Dermatology", IN International Surg: 47⁶: pp. 528–534, 1967.

*Primary Examiner*—Channing L. Pace
*Attorney, Agent, or Firm*—David A. Burge Co.

[57] ABSTRACT

A cryogenic apparatus including a highly versatile probe with a deformable tip, and cryogen supply systems for delivering cryogen to the probe. The probe includes a tubular stem with a resilient mass of porous material such as copper mesh positioned adjacent one end of the stem. A thin cryogen impervious membrane such as latex or silicone rubber extends around the porous mass and around the adjacent stem end region. The membrane and the porous mass together form a deformable tip which can be shaped to almost any desired configuration. Cryogen introduced into the stem penetrates the porous mass but is confined by the membrane so it does not come in direct contact with selected surface areas being treated. A dispenser bottle cryogen supply system is provided for introducing cryogen into the probe stem. Alternate continuous flow cryogen supply systems are provided which permits probe use in any attitude of inclination.

Novel cryosurgical methods employing the apparatus are described which illustrate the versatility of the improved system.

32 Claims, 12 Drawing Figures

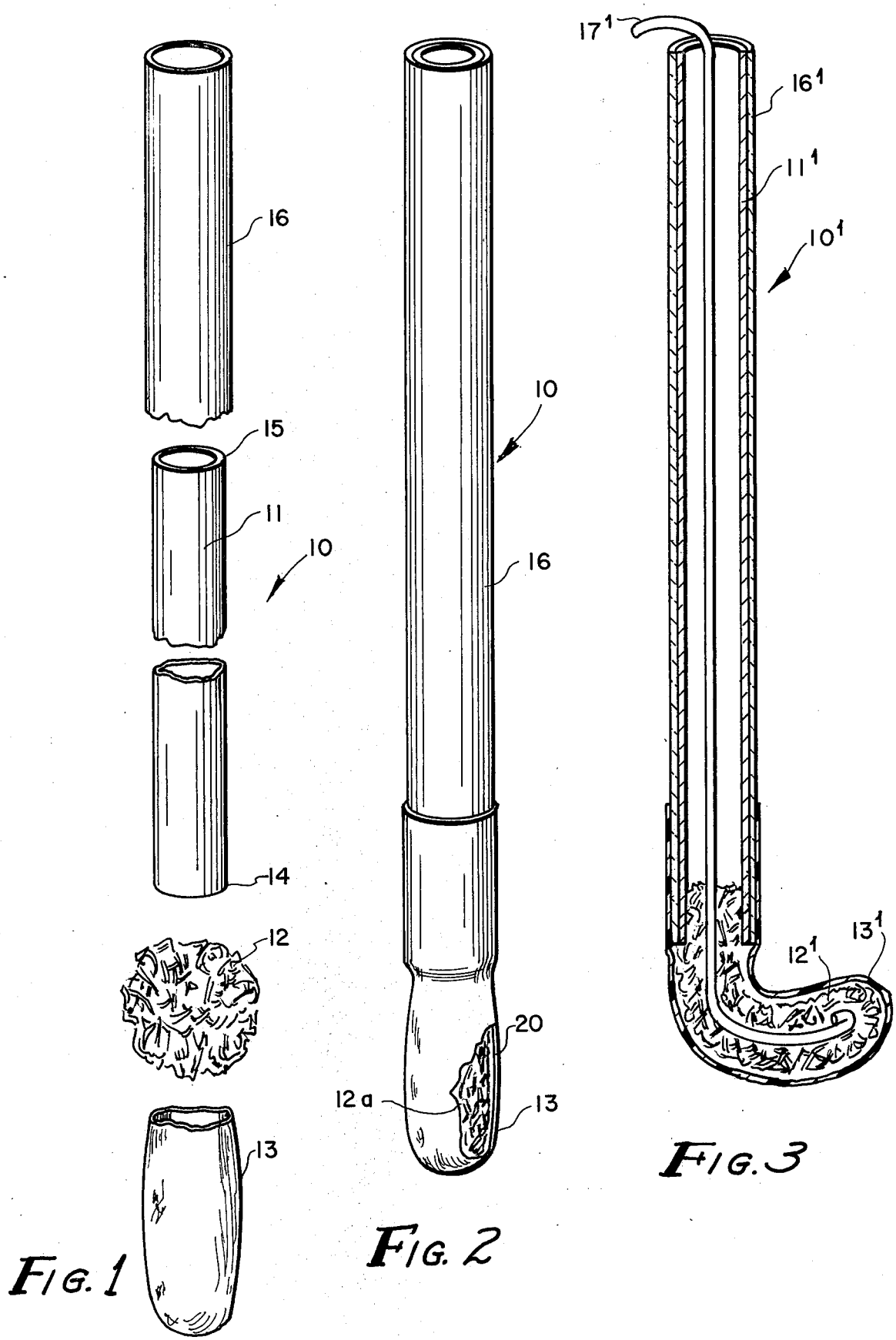

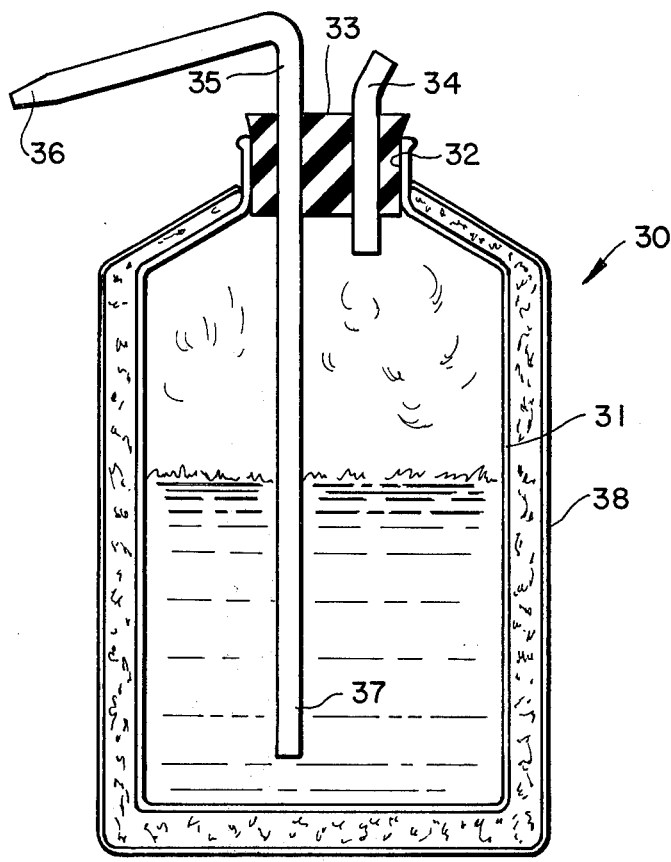
FIG. 4
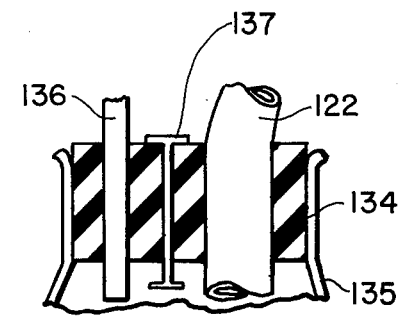
FIG. 6
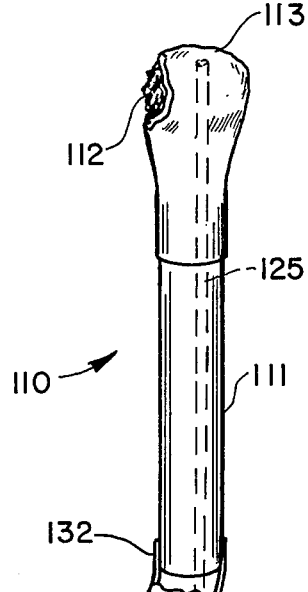
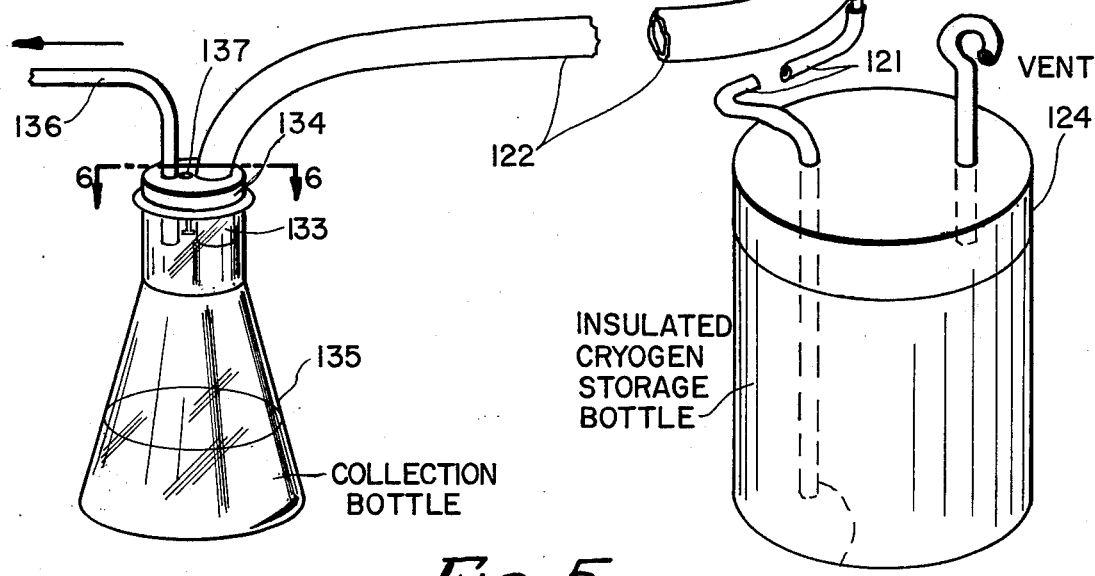
FIG. 5

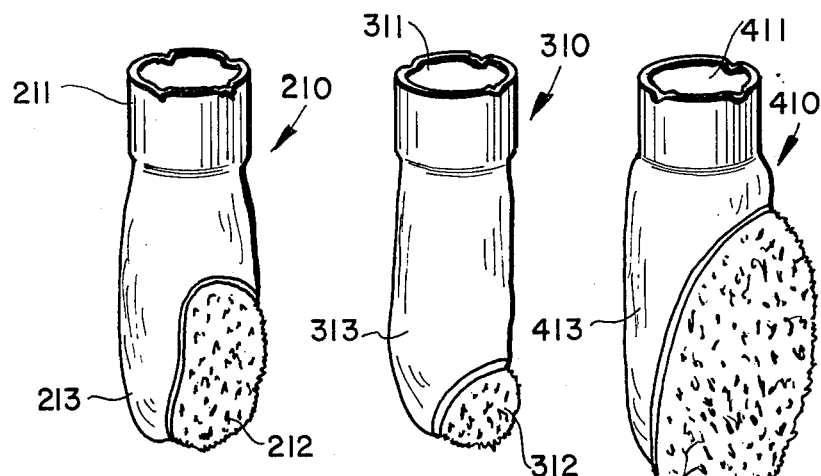
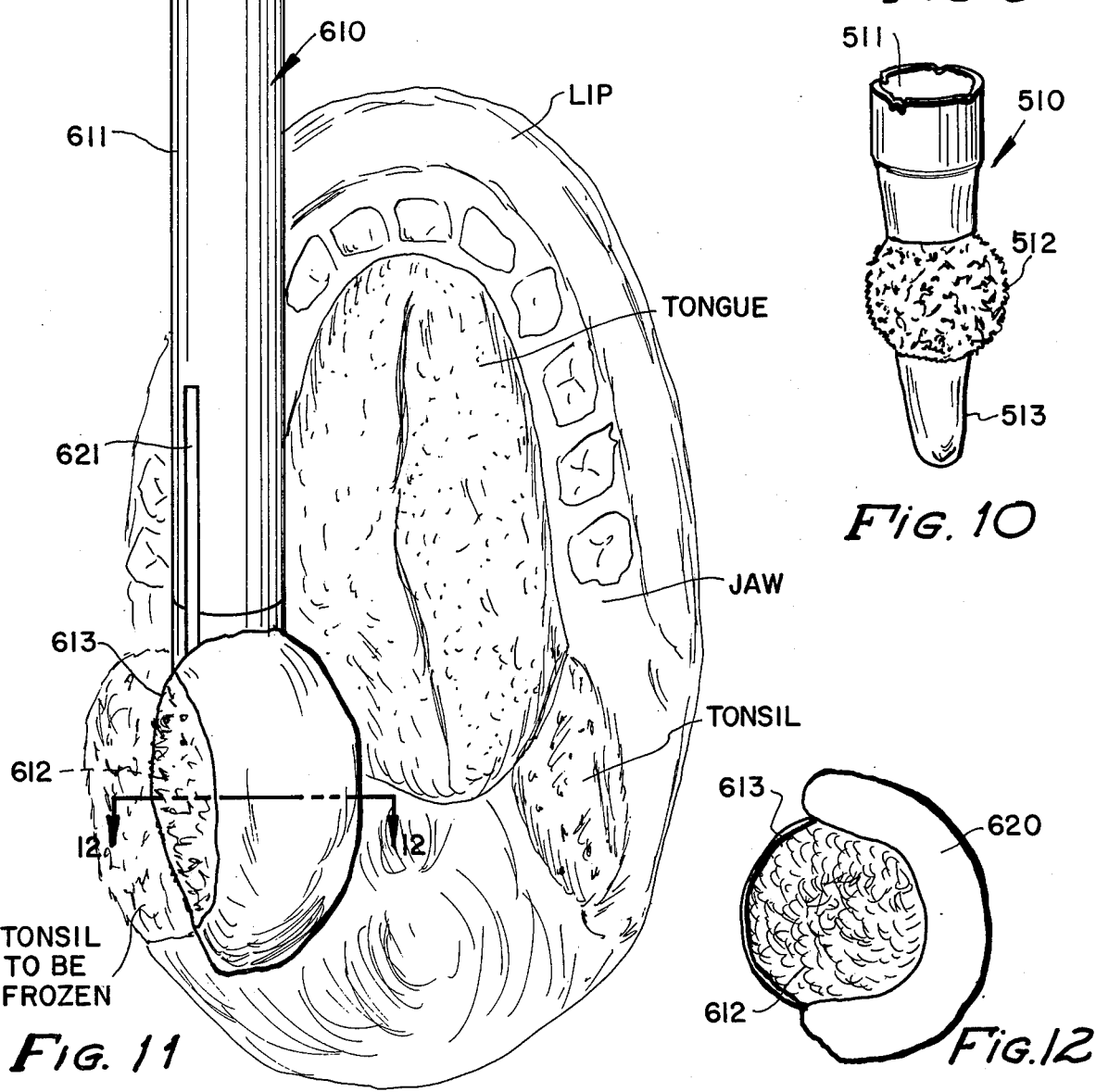

CRYOSURGICAL SYSTEM

BACKGROUND OF THE INVENTION

1. Field of the Invention

The present invention relates generally to cryogenic systems and more particularly to a cryogenic system for cooling selected surface areas in a safe, carefully controlled manner. While the highly versatile system of the present invention has many non-medical uses in super-cooling selected surface areas, in cryo-adhesion, cryo-fragmentation, cryo-solidification of liquids, the like, and an important application is in the medical field of cryosurgery.

2. Prior Art

The term "cryosurgery" relates broadly to a wide variety of surgical procedures wherein tissues are selectively destroyed by freezing with cryogenic materials.

While cold temperatures were reportedly used as early as the 1850's in the treatment of such diseaases as cancer, significant medical use of cryogens did not occur until the 1890's. Processes for liquifying air were developed a early as 1877, but the new product did not come into broad use until the vacuum insulated cryogen storage vessel was developed nearly 15 years later.

Liquid air continued to be the principal liquified gas cryogen in medical use until the 1940's when liquid nitrogen become available. Liquid nitrogen is preferable to liquid air and most other liquified gases for medical uses because it does not support combustion. It continues to be the preferred cryogen for most medical purposes not only because it is available very economically, but also due to its very high latent heat of vaporization. Whereas, other available non-flammable cryogens such as $CO_2$, $N_2O$ and freon change phase at $-90°$ centigrade or above, liquid nitrogen changes phase at $-196°$ centigrade. The resulting extraordinary latent heat of vaporization makes liquid nitrogen of unique value in effecting a fast deep penetrating freeze in diseased tissues.

Four cryogenic treatment techniques have been used with success:
1. The swab method;
2. The spray method;
3. The open probe method; and
4. The closed chamber probe method.

The swab method utilizes a swab such as a wooden stick with cotton tightly twisted around one end to form an absorbent tip. The cotton covered tip is dipped in a cryogen and then is placed on the tissue to be treated. This direct application technique is not well adapted for use with liquid nitrogen to treat large tissue areas or to effect deep penetration freezing.

The spray method is another direct application technique where a cryogen mist is sprayed onto the tissue to be treated. This technique is commonly used with liquid nitrogen to thinly freeze broad surface areas. It can also be used to obtain substantial depth of penetration with prolonged application. The spray method has several drawbacks including difficulty in achieving uniformity of penetration and in controlling the deflection of cryogen droplets from the primary target. These drawbacks render the spray technique for intra-cavity use and for discrete site freezing-in-depth to controlled limits.

The open probe method utilizes a tubular probe having an open applicator end which is pressed into surrounding engagement with a tissue surface to be treated. The tissue closes the applicator end and cooperates with the tubular wall of the probe to define a chamber into which liquid cryogen is introduced for direct application to the tissue. During cryogen application, the tissue freezes firmly to the end of the probe.

The closed chamber probe method typically provides a probe structure having a relatively rigid tip cooled internally by cryogenic exposure. It differs from the swab, spray, and open probe methods, in that the cryogen itself is not brought into contact with the tissue to be treated. This better enables the probe to be used in intra-cavity applications. Sufficient accuracy is attainable to enable discrete site freezing-in-depth. The closed chamber probe has even been used in microsurgery.

The freezing process is typically monitored by carefully observing its progress as indicated by changes of color and texture of tissues. Needle-like thermistor units implanted in the tissues to be frozen are also used on occasion to provide a more exact indication of temperature changes as they occur.

The depth, extent and rate of freezing achieved with any cryoprobe system depends on several factors, including the type of cryogen used, the area of contact between the cyroprobe and the target tissue, and the time during which the tissue is exposed to cryogen cooling. Other factors which also come into play include the rate at which cryogen is supplied to the probe tip, and the efficiency of the probe in transferring heat out of the tissue and into the cryogen. Since the target tissues freeze rigidly to the probe tip during treatment and the probe-to-tissue contact cannot be disrupted reliably without thawing, the freezing process is controllable chiefly by regulating the supply of cryogen to the probe tip.

Early cryoprobes used in the 1900's included cylindrical and spherical applicators made of glass or brass which were filled with liquid and rolled over to the tissues to be treated. More sophisticated probes were developed together with more precise instrumentation in the early 1960's through the work of Dr. I. S. Cooper. The Cooper system employed a cannula about 2.2 mm. in diameter which was vacuum insulated except for the tip. The temperature of the tip was monitored by a thermocouple control system which regulated the flow of liquid nitrogen to the cannula.

While various types of control system are known for regualting the flow of cryogen to the tip of a probe, most of these known systems have valves or other controls located at some distance from the site of freezing. Adjusting the flow of cryogen during surgery accordingly requires that apparatus outside the surgical field be manipulated. This is undesirable not only because it is often inefficient and clumsy, but also because time delays are involved in effecting the adjustments and before uniform cryogen flow is re-established at the newly adjusted setting.

Still another problem with known and proposed cryoprobes is that they typically employ relatively rigid tips or applicator surfaces which rarely conform with the tissue surfaces to be treated. The accepted solution has been to design a wide range of specialized probe configurations and to select the most appropriate available probe for surgical use. Maintaining a large probe inventory is a costly undertaking which is often frustrated by non-conformance of available probe shapes to the highly irregular and randomly variable shapes of tissue surfaces.

Most known probes cannot be reshaped due to the rigid nature of the materials from which they are constructed. Most probes are also provided with directed cryogen flow paths which become disrupted if the probe is deformed, thereby rendering the probe unusable.

The use of a thin, softly compliant sleeve or membrane supported on a hard foamed plastic or metallic probe body is proposed in U.S. Pat. No. 3,421,508 issued Jan. 14, 1969, to F. L. Nestrock. The applications to which the Nestrock probe can be put are severely limited by the relatively rigid nature of the probe. It cannot be reshaped by hand prior to use. The resilience of the probe is limited to the resilience of the outer membrane or sleeve, and as such is not readily deforamble to accommodate substantial tissue surface irregularities. The cryogen flow path through the probe tip requires a remotely controlled flow which is dependent upon the cryogen supply system design. The need for a carefully controlled cryogen flow through the probe severaly limits the selection of probe sizes and shapes which can be used without redesigning the cryogen supply system. Moreover, the multi-part precision machined nature of the probe assembly result in a very costly medical apparatus.

SUMMARY OF THE INVENTION

The present invention overcomes the foregoing drawbacks of the prior art and provides an improved highly versatile cryogenic system having a wide variety of applications. When used in cryosurgery, the system permits the selective freezing of tissues in a safe, controlled manner. It combines the most desirable features of the spray and probe methods, and extends their utility.

An improved cryoprobe is provided having a tip which can be deformed to almost any desired configuration prior to the probe's being filled with a cryogen, such as liquid nitrogen. The probe includes three major parts: a tubular stem, a resilient porous mass of intertwined or mesh-like material, and a membrane.

The porous mass is formed into a ball and positioned adjacent one end of the tubular stem. The membrane is positioned over the mass and over the adjacent stem end region and compressively engages both the mass and the stem end region to secure the mass to the stem.

The tubular stem serves as a handle which can be grasped by a physician to position the probe tip and press it in place against tissue to be treated. The stem also serves as a reservoir for cryogen. The stem is typically formed from a cold fracture resistent plastic tube. An insulative sheath of styrofoam or the like is wrapped around the tube to protect the physician's hand from cold temperature cryogen within the tube.

The porous mass preferably comprises a good heat conductive metal such as copper, aluminum or silver, but can comprise non-conductive materials such as nylon, dacron and polyethylene. The mass is highly porous to provide a densely interconnected array of flow paths for transmitting liquid cryogen to the membrane, and for permitting the escape of cryogen gas from the membrane surface back into the stem of the cryoprobe. The mass should also be deformable without destroying its porosity, and resilient after deformation. The preferred material for forming the mass is an intertwined mesh of copper ribbon such as is used in a number of commercially available scouring pads.

The membrane comprises a thin pliable material which preferably has a finger-shaped configuration. A preferred material for forming the membrane is silicone rubber which resists deterioration with age and can be autoclaved. An acceptable material is latex rubber of the type commonly used in a surgeon's glove. The membrane cryogen from the tissues being treated, and yet it must be thin enough to permit efficient heat transfer. Both latex and silicone rubber are acceptable in that they do not become excessive brittle at subzero temperatures and can be reused repeatedly. They thaw and regain elasticity quickly after profound freezing and they are easily detached from frozen tissue. Moreover, they are sufficiently transparent to permit visualization of the boiling action of the cryogen in the copper mesh, thereby permitting visual monitoring of the cryogen supply.

An insulation barrier of preselected shape can be interposed between the copper mesh and the surrounding membrane to limit the size of the copper mesh applicator surface, and to provide an area which can safely be engaged by the physician's hand in exerting pressure on the probe tip. By this arrangement, normal tissues surrounding tissues to be treated can be protected from the freezing action of the cryogen. Any portion of the probe tip can be insulated, and the insulation can be postioned externally as well as internally of the membrane. A flexible styrofoam insulating material is preferred, but other types of insulation can be used.

The membrane can also be provided with a closed inflatable air-bag or compartment. When inflated, the air-bag can serve the dual functions of insulating selected regions of the probe tip from tissues in the vicinity of the target tissues, and of assisting in thrusting the uninsulated tip portions into firm engagement with the target tissues. Such inflatable probes are advantageously used in difficult to expose regions such as the throat and the colon. They can be inserted while deflated and then inflated to effect proper positioning.

Probe tips of a variety of sizes can easily be constructed by adding or subtracting porous material. Probe tips of almost any desired shape can be fashioned from the porous mass, thereby giving the probe great versatility of use.

One or more semi-rigid preshaped rods or tubes extending from within the tubular stem into the porous mass can be used to help maintain the desired configuration of the tip and to provide a means of pressing the probe tip into engagement with tissues. These rods or tubes are preferably, but not necessarily, formed from a heat conductive malleable material such as copper or aluminum. The rods or tubes are necessary in some applications where the target surface is the curved wall of a channel or cavity not offering wide areas of access. In such applications the probe tip requires auxiliary support to permit its being pressed firmly against tissue to be treated. A tube used in this manner, may also serve as a cryogen conduit to the probe tip.

In use the cryoprobe tip is preshaped to a desired configuration and is then pressed into position aginst the tissues to be treated. Sufficient pressure is ordinarily used to inhibit warm blood flow within the tissues, whereby the tissues can be more quickly frozen. As the probe tip is pressed in place, the resilience of the porous mass permits it to conform to tissue surface irregularities thereby obtaining an optimal conductive heat transfer juncture with the tissues.

Once the tip is pressed into place, cryogen is introduced into the stem of the probe and into the porous mass. The porous mass cools quickly and heat transfer from the tissues being treated begins promptly. The freezing cycle continues for several minutes whereafter the tissues are allowed to thaw. The freezing cycle is ordinarily repeated at least once to assure that all living cells in the target area have been damaged.

The destruction of tissues by freezing has several advantages over other approaches. First, the cold temperatures tend to deaden local nerve endings with the result that the patient is subjected to less pain both during and after the treatment. Second, the freezing process can be used to treat growths around large blood vessels with greater safety than other methods. In such situations as where a tumor has developed around an artery in the neck, burning or cutting out the tumor may cause the artery to rupture. This is not as likely to happen with freezing, so the risk to the patient is less.

Third, in some instances, diseased bone tissues can be salvaged. For example, where a portion of a jawbone is diseased, it is customary to saw out the diseased portion and either leave a defect, or substitute a bone graft or a metal plate. With cryogenic freezing, the cells in the diseased area of the bone can be killed and the bone left structurally intact, thereby eliminating the need for a bone graft or a metal plate. The dead bone will very gradually be replaced by new bone growth.

In accordance with another aspect of the present invention, two types of cryogen supply systems are provided for feeding cryogen to the probe. One system provides a cryogen dispenser which is used to fill the stem of the cryoprobe where the probe will be used in a tip-down attitude. The other system is a continuous flow system for supplying cryogen to the porous mass of a probe tip where the probe is used at any angle of inclination from a tip-down attitude to a tip-up attitude.

The dispenser bottle supply system comprises an insulated cold-fracture resistent plastic bottle with a neck opening closed by a two-hole stopper. A short vent tube extends through one hole of the stopper and into the upper inner region of the bottle. A longer dispensing tube extends through the other hole of the stopper and into the lower inner region of the bottle.

The bottle is prepared for dispensing by filling it with liquid cryogen, and securing the stopper in place such that the dispensing tube extends into the liquid cryogen. With the vent tube open, the gas generated by the bubbling, boiling cryogen escapes to the atmosphere. Dispensing is achieved simply by blocking the vent tube, whereupon gas pressure builds up in the bottle and forces liquid cryogen out the dispensing tube.

One advantage of the cryogen dispenser bottle is its simple design and very low cost. Another advantage is that it can be held in one hand and operated simply by placing the index finger of the same hand over the vent tube. Before and after use, the dispenser bottle can be stored in a ready location, typically on a surgical instrument table. Still another advantage is the safety and accuracy with which cryogen dispensing can be performed. The dispensing action ceases abruptly once the vent tube is open, enabling carefully controlled quantites of cryogen to be dispensed without danger of spillage.

The continuous feed supply system utilizes the same sort of cryoprobe structure described above. Dual flexible conduits communicate with the probe stem. One of the conduits delivers cryogen to a position adjacent the porous mass. The other conduit connects with a vacuum source for evacuating the probe stem. By controlling the vacuum evacuation of the stem, a continuous supply of cryogen can be drawn through the supply tube and discharged into the porous mass, thereby enabling the probe to be used at any angle of inclination from tip-down to tip-up attitudes.

The dispenser bottle system can be converted to a continuous feed system for use with small sized probes. Dual conduits communicating with the probe stem are provided with one extending into the cryogen supply of the dispenser bottle, and the other either open to the atmosphere, or connected to a collector bottle which is open to the atmosphere. When the dispenser bottle vent opening is closed, pressure build-up within the dispenser bottle forces cryogen into the probe. The membrane covering larger sized cryoprobes can inflate and/or rupture with excessive nitrogen gas pressure in the initial phase of activation, if due care is not exercised in the use of this method.

The improved cryoprobes of the present invention add versatility to known cryosurgical techniques since the probe tip can be formed to almost any desired shape. The cryogen supply systems provide simple and inexpensive means for supplying cryogen in a safe, controlled manner to the probe.

Multiple target areas and excessively large target areas can be treated through the simultaneous use of multiple probes. While known cryoprobe supply systems are specially designed to accommodate a single probe of a specific type, the supply systems of the present invention can be used simultaneously with multiple probes of different sizes and configurations to dispense cryogen from a single source.

As will be apparent from the foregoing, it is a general object of the present invention to provide a novel and improved cryogenic system including cryogenic apparatus and techniques employing it.

Other objects and a fuller understanding of the invention may be had by referring to the following description and claims taken in conjunction with the accompanying drawings.

DESCRIPTION OF THE DRAWINGS

FIG. 1 is an exploded view of one probe embodiment of the present invention;

FIG. 2 is a perspective view of the probe of FIG. 1 when assembled;

FIG. 3 is a cross-sectional view of another probe embodiment;

FIG. 4 is a cross-sectional view of one embodiment of a cryogen dispenser for supplying liquid cryogen to the probes of FIGS. 1–3;

FIG. 5 is a schematic perspective view of still another probe embodiment coupled to a vacuum flow cryogenic supply system;

FIG. 6 is an enlarged cross-sectional view of a portion of the collection bottle used in the system of FIG. 5, as seen from the plane indicated schematically by the line 6—6 in FIG. 5;

FIGS. 7–10 are perspective partial views of typical alternate probe tip configurations;

FIG. 11 is a schematic illustration of still another probe embodiment as employed in the throat of a patient to freeze a tonsil; and FIG. 12 is a cross-sectional view of the probe of FIG. 11 as seen from the plane indicated by the line 12—12 in FIG. 11.

DESCRIPTION OF THE PREFERRED EMBODIMENT

Referring to FIGS. 1 and 2, a cryoprobe constructed in accordance with the present invention is shown generally at 10. The cryoprobe includes a supporting tubular stem 11, a flexible porous mass of intertwined or mesh-like material 12, and a thin pliable finger-shaped membrane 13. The stem 11 has open end regions 14, 15.

In assembly, the porous material 12 is formed into a ball-shaped mass positioned adjacent the lower end region 14 of the stem 11. The membrane 13 is drawn over the porous mass 12 and onto the stem end region 14. The membrane 13 is resilient and compressively engages the porous mass 12 and the stem end region 14. An insulating sheath 16 is wrapped around the stem 11 and adhered in place to provide a handle structure that can be safely held by a physician when liquid cryogen is present inside the stem.

The stem 11 serves at least four functions. First it provides a relatively rigid support for the cryoprobe tip and serves as a handle to position and guide the tip. Second, it provides a conduit for channeling liquid cryogen from the upper end region where it is introduced into the stem, to the lower end region where it is delivered to the porous mass 12. Third, it serves as a cryogen reservoir and is typically filled with cryogenn to about one-half of its capacity when the cryoprobe is in use. Finally, it serves as an exhaust conduit for cryogen gas.

The stem 11 is preferably formed from a relatively rigid tube of plastic material such as polyethylene or polypropylene. It can be formed of other materials such as paper, wood, photographic film or other materials which do not tend to crack or become dangerously brittle during the temperature change which takes place when the stem is filled with liquid nitrogen.

The insulative sheath 16 preferably comprises a thin sheet of styrofoam which is wrapped around the stem 11 and is adhered in place. Other conventional insulative materials such as glass wool, multiple layers of paper or plastic film, etc. can be used. The insulative sheath 16 can also be formed integrally with the stem 11. The sheath 16 should provide sufficient insulation to protect the hands of a physician from the low temperature cryogen within the stem 11, but should not be so bulky as to add unnecessarily to the size or weight of the cryoprobe 10.

The porous mass 12 serves at least three functions. First, it provides a densely interconnected array of flow paths for the delivery of liquid cryogen to regions near the membrane 13 and for simultaneous escape of cryogen gas formed by evaporation. Second, it provides a readily deformable supporting tip structure which can easily be shaped to a desired configuration prior to use, thereby giving the cryoprobe great versatility of shape. Third, it provides a resilient tip structure which, even after it has been deformed to a desired shape, is still sufficiently resilient to conform to tissue irregularities.

The porous mass 12 serves still another function where the material from which it is formed has a high coefficient of heat transfer, as with such materials as copper, aluminum and silver. The good heat conductivity of such materials enables the mass to assist in maintaining a uniform temperature gradient at all points along the surface of the membrane 13.

The material from which the mass 12 is formed presents a highly porous array of random flow paths to the cryogen. It is the multi-directional interconnected nature of these flow paths which permits the mass to be substantially deformed and preshaped without losing its ability to supply cryogen to the membrane surface. The mass 12 must also be formed from materials which are not so pointed or so rigid as will puncture the membrane 13.

Non-conductive materials such as wool, cotton, nylon, polyester, polyurethane, etc. can be used to form the mass 12, particularly where the stem 11 is held vertically with the mass 12 at the lower end so the mass is effectively filled with cryogen due to gravitational forces. In such instances as will later be described where the probe tip must be held above the stem 11 during use and cryogen is continuously sprayed into the mass 12, the mass 12 is preferably formed from highly conductive materials such as copper or aluminum to assure that the cold temperatures are transmitted to the membrane surface. Mixtures of metallic and non-metallic porous materials may be utilized as well.

The membrane 13 serves at least three functions. First, it acts as a means for securing the porous mass 12 to the stem 11. The membrane 13 compressively engages the stem end region 14 and holds the mass 12 in place adjacent the stem 11. Second, the membrane isolates the cryogen from tissues being treated while not appreciably impairing the transfer of heat from the tissues to the cryogen. Third, the pliability of the membrane 13 adds to the resilience of the cryoprobe tip thereby facilitating the ability of the tip to conform to tissue irregularities. Where the membrane 13 is formed of substantially transparent material, it serves the added function of permitting visual monitoring of the cryogen boiling which takes place within the mass 12.

The preferred material from which the membrane 13 is formed is pure latex rubber of the type used in a surgeon's glove. A surgeon's glove finger has been found to form a very acceptable membrane. Other latex rubber finger-shaped membranes are commercially available in the form of finger cots. While materials other than latex rubber can be used, vinyl materials and the like have been found to provide a less efficient heat transfer medium, and to exhibit excessive cold fragility and inferior resistance to puncture.

The thickness of the membrane 13 has been found to be of significant importance. Membranes of about one-half mil (i.e., about 0.013 millimeter) work significantly better than membranes of one mil thickness in that they permit a significantly faster, more efficient heat transfer.

It is also important that the membrane not become brittle at low temperatures and that it be reusable repeatedly. Latex rubber has these properties and is also desirable from the viewpoint of its ability to regain elasticity quickly after profound freezing, whereby it is easily and safely detached from frozen tissue.

It is frequently desirable to insulate certain regions of the cryoprobe tip (1) to confine extraction of heat to selected tissue areas; (2) to prevent accidental damage to nearby tissues which may unintentionally come into engagement with the cold probe tip; and (3) to provide an insulated backing on the probe which can be safely touched by a physician in pressing the probe tip into the firm engagement with tissues being treated. Any portion of the probe tip can be insulated, and the insulation can be positioned internally or externally of the membrane 13. A flexible styrofoam insulating material is preferred because a thin sheet can be used effectively without adding significantly to the size of the cryoprobe tip.

Referring to FIG. 2, a sheet of styrofoam insulation 20 is shown interposed between portions of the porous mass 12 and the membrane 13. The styrofoam sheet 20 encircles most of the perimeter of the porous mass 12, leaving only an applicator region 12a exposed for use.

A significant feature of probes constructed in accordance with the present invention is that the size of the probe tip can be increased or decreased simply by adding more porous material to the mass 12, or removing some porous material from the mass 12. The volume of the mass does not appreciably affect the random flow characteristics of the cryogen. Larger masses do consume more cryogen in the initial process of decreasing their temperature, but once the mass is cooled, probe operation tends to be the same whether the mass is relatively large or small, providing cryogen supply is maintained. Larger probes will, of course, consume more cryogen than do smaller probes.

Referring to FIG. 3, an alternate probe embodiment is shown generally at 10' as including a stem 11', a porous mass 12' and a membrane 13'. The probes 10, 10' differ principally in that (1) the porous mass 12' is of larger size than the porous mass 12; (2) the porous mass 12' is of curved configuration as opposed to the relatively straight configuration of the mass 12; and, (3) a metallic rod 17' extends through the stem 11' and into the porous mass 12' to assist in maintaining the mass 12' in a curved configuration.

The metallic rod 17' does not interfere with the flow of cryogen through the mass 12'. It helps maintain the curved configuration of the mass 12' and if extended out the upper end region 15' of the stem 11' can provide a means for manipulating the probe tip and for applying pressure to the tip.

Referring to FIGS. 5 and 7-10, still other alternate probe tip embodiments are shown at 110, 210, 310, 410, 510 as including stems 111, 211, 311, 411, 511 and porous masses 112, 212, 312, 412, 512 surrounded by membranes 113, 213, 313, 413, 513. Insulation sheets are provided between these membranes and portions of the porous masses to expose selected applicator areas of the porous masses.

In use, the cryoprobe tip is first shaped to the general configuration of the surface of the tissue to be treated. The tip is then pressed into engagement with the tissue. A sufficient amount of pressure is, in most instances, used to shut off the normal blood flow to the tissue being treated, and to drive out the blood that is initially in the tissue. Once this is done, cryogen is introduced into the cryoprobe and the process of freezing the tissue begins. Cryogen is introduced into the stem until the stem is about half full. The freezing process progresses typically for about 2 to 5 minutes, whereafter the tissues are permitted to thaw for about 2 to 5 minutes. Ordinarily at least a second freezing cycle is used to assure that no uninjured cells remain in the target area. While cell death is not assured by freezing, it becomes highly probable if cell temperature drops below about −40° C.

During the freezing process, the cryogen bubbles and boils audibly within the stem of the cryoprobe. As the supply of cryogen is depleted, the bubbling action in the area of the copper mesh can be observed to cease.

After the treated tissues have been frozen at least twice, they are ordinarily left alone for about 5-10 days. During this time, the tissues ordinarily go through a process of discoloring to a blue or black color. The tissues ordinarily swell taking on fluid, but eventually the swelling regresses and the tissues wither away. In some instances, th dead tissue is surgically removed several days after it has been frozen. Biopsies are then taken of the surrounding living tissue to assure that all the diseased tissue has been killed. If additional living diseased tissue is found, it is frozen and removed.

Referring to FIG. 4, a cryogen dispenser for introducing liquid cryogen into the stem 11 of a cryoprobe is shown generally at 30. The dispenser comprises a cold-fracture resistant plastic bottle 31 having a neck opening 32 closed by a two-hole stopper 33. A short gas vent tube 34 extends through one hold of the stopper 33 and communicates the upper interior region of the bottle with the atmosphere. A longer curved or bent tube 35 extends through the other hole of the stopper 33. The upper end region of the tube 35 is formed into a nozzle shaped configuration 36. The lower end region 37 of the tube 35 extends into the lower interior region of the bottle 31. An insulative jacket 38 is provided around the bottle 31. The jacket preferably comprises glass fiber wool with an insulating tape cover.

In use, the stopper 33 is removed from the neck opening 32 and the bottle 31 is about half filled with liquid cryogen. The stopper 33 is then replaced. The short vent tube 34 permits cryogen gas to escape from the upper interior region of the bottle. The longer dispensing tube 37 extends into the liquid cryogen supply.

The cryogen is dispensed simply by closing off the vent tube 34. Typically, a physician holds the dispenser 30 in his hand and places his index finger over the upper end of the vent tube 34 to initiate cryogen dispensing. With the tube 34 closed, the gas released from the bubbling cryogen into the upper inner region of the bottle 31 creates a positive pressure which forces liquid cryogen up through the dispensing tube 35 and out the nozzle 36. This dispensing action can be stopped almost instantaneously by opening the vent tube 34.

It is not always possible to use the cryoprobe 10 in an erect, tip-down attitude. In some surgical applications, the probe must be used substantially horizontally and even vertically in a tip-up attitude. Where this is the case, a continuous flow cryogen supply system is used to deliver cryogen to the porous mass 12 of the cryoprobe tip.

Referring to FIG. 5, the cryoprobe 110 can be used at substantially any angle of inclination from tip-down to tip-up attitudes. As has been explained, the cryoprobe 110 is structurally identical to the probe 10 in its inclusion of a stem 111, a porous mass 112, and a membrane 113.

A supply tube 121 and an exhaust tube 122 communicate with the probe 110. The supply tube 121 has one end region 123 extending into a supply of liquid cryogen stored in a conventional thermo-insulated cryogen reservoir bottle 124. The other end region 125 of the supply tube 121 extends through an aperture 120 in the exhaust tube 122 and into the porous mass 112 to a position near the inner surface of the membrane 113. The supply tube 125 may also function as the equivalent of metallic rod 17' shown in FIG. 3.

The exhaust tube 122 has one end region 132 which extends over the end of the stem 111 in sealing engagement therewith. The exhaust tube 122 is larger in diameter than the supply tube 121 to prevent clogging by ice formations, and comprises a tube which is flexible but which is also resistant to collapse when vacuum evacuated. The other end region 133 of the exhaust tube 122 extends through a stopper 134 and into a liquid trap or collection bottle 135. A vacuum source conduit 136 also extends through the stopper 134 into the collection bottle 135. A pop-up pressure valve 137 is provided in the stopper 134, as shown in FIG. 6, to prevent pressure buildup which could otherwise occur when the collection bottle 135 is not being vacuum evacuated.

In operation, the vacuum conduit 136 is connected to a vacuum source (not shown). As a vacuum develops within the trap 135, the tube 122, the stem 111, and the tube 121, liquid cryogen is drawn through the tube 121 and discharged into the porous mass 112. Cryogen continues to flow into the mass 112 as long as the vacuum is maintained. Any liquid cryogen which enters the vacuum tube 122 will drip into the trap 135 where it will evaporate.

Since the supply system of FIG. 5 is a closed continuous supply system, the probe 110 can be inverted or used at any required angle without the danger of spilling cryogen.

The dispenser bottle 30 can be converted to a continuous feed dispenser system for use with relatively small probes. The conversion is accomplished simply by connecting the dispensing tube 35 to a closed probe supply tube such as the tube 121 on the probe 110. Dispensing is then effected simply by closing the vent tube 34, whereby pressure buildup in the bottle 30 will feed cryogen to the probe. This type of dispensing system can be used without assistance of a vacuum evacuation apparatus, or can be used to augment cryogen supply in vacuum evacuated systems.

Referring to FIGS. 11 and 12, still another probe embodiment 610 is shown which has advantageous application in hard-to-reach areas such as the throat and colon. In the manner of the above described probes, the probe 610 includes a stem 611, a porous mass 612 and a membrane 613. The principal difference between the probe 610 and previously described probes is that the membrane 613 is specially formed to include a close inflatable compartment or air-bag 620. A tube 621 communicates with the compartment 620 for admitting and discharging air.

As shown in FIG. 11, the probe 610 is well adapted for use in freezing tonsil tissues. It is positioned in the throat of a patient with the air-bag 620 deflated. When in position, the air-bag 620 is inflated by compressed air supplied through the tube 621. The inflation of the air-bag 620 insulates the porous mass 612 from tissues around the tonsil tissues being treated, and helps to press the porous mass 612 into firm mating contact with the tonsil tissue.

After the tonsil tissue has been frozen, the air-bag 620 is deflated to reduce the size of the probe tip, whereafter the probe 610 is withdrawn from the patient's throat.

Although the invention has been described in its preferred form with a certain degree of particularity, it is understood that the present disclosure of the preferred form has been made only by way of example and numerous changes in the details of construction and the combination and arrangement of parts may be resorted to without departing from the spirit and scope of the invention as hereinafter claimed.

What is claimed is:
1. A cryoprobe comprising:
 a. a supporting structure
 b. a deformable tip carried by said structure;
 c. said tip including a porous mass which is deformable to conform substantially to the contour of a surface to be treated, and being capable following deformation to substantially retain its deformed configuration for use;
 d. a cryogen-impervious membrane sheathing the mass;
 e. the mass defining interconnected spaces for transmitting cryogen to the inner surface of the membrane; and,
 f. said membrane being operative to retain cryogen within said tip.

2. The apparatus of claim 1 wherein said probe includes a cryogen supply conduit adapted for connection to a source of cryogen for supplying cryogen from said source to said porous mass.

3. The apparatus of claim 2 wherein said conduit forms a part of said supporting structure, a cryogen reservoir is defined within said supporting structure, and said conduit is operable to duct cryogen from said reservoir to said porous mass.

4. The apparatus of claim 2 wherein said supporting structure and said membrane cooperate to define a vacuum evacuable chamber with said porous mass enclosed therein, said conduit is adapted for connection to a source of cryogen external to said chamber and extends into said chamber to supply cryogen thereto from said external source, and connection means is provided to communicate said chamber with a vacuum whereby a vacuum drawn in said chamber will effect a supply of cryogen from said external source to said chamber.

5. The apparatus of claim 1 additionally including insulation means carried by said tip in surrounding relationship to portions of said porous mass for insulating said portions thereby reducing the effective applicator area of said membrane.

6. The apparatus of claim 5 wherein said insulation means includes an inflatable expansible chamber formed on said tip adjacent portions of said porous mass.

7. The apparatus of claim 6 wherein portions of said membrane define said inflatable chamber.

8. The apparatus of claim 5 wherein said insulation means is interposed between said membrane and said porous mass.

9. The apparatus of claim 1 additionally including insulation means interposed between portions of said membrane and portions of said porous mass to limit the effective applicator surface area of said probe.

10. The apparatus of claim 9 wherein selected portions of said insulation means are inflatable.

11. The apparatus of claim 1 wherein said supporting structure includes a tubular member defining an exhaust opening at one end thereof, and a cryogen supply tube extends through said exhaust opening and into said porous mass for supplying cryogen to said porous mass, said exhaust opening providing a means of escape for cryogen gas emerging from said porous mass.

12. The apparatus of claim 1 wherein said porous mass comprises a good heat conductive material whereby said porous mass facilitates establishing and maintaining a uniform temperature gradient along membrane portions which contact said porous mass.

13. The apparatus of claim 12 wherein said conductive material is selected from the group of metals comprising copper, aluminum, silver and gold.

14. The apparatus of claim 1 wherein said membrane is of generally finger-shaped configuration and compressively engages portions of both said porous mass and said supporting structure.

15. The apparatus of claim 1 wherein said membrane is an elastomeric casing which can assume a plurality of shapes complementary to the shape of said porous mass.

16. The apparatus of claim 1 additionally including at least one rigifying member adjacent said porous mass to increase stability of the mass and prevent its deformation beyond tolerable limits when pressed in place against tissues to be treated.

17. A cryosurgical apparatus comprising:
   a. a probe positionable in contact with a surface of tissues to be frozen and including:
      i. a supporting structure;
      ii. a resilient deformable porous mass of material carried by said structure and defining closely arranged interconnected flow paths for cryogen, said porous mass being deformable to provide outer surface portions which substantially conform to the contour of a surface to be frozen and being capable following deformation of substantially retaining its deformed configuration for use;
      iii. a cryogen-impervious membrane stretched over said outer surface portions of said mass and capable of retaining liquid cryogen within said mass; and,
   b. cryogen supply means for supplying cryogen to said porous mass.

18. The apparatus of claim 17 wherein said supply means includes a cryogen reservoir formed within said supporting structure in communication with said porous mass.

19. The apparatus of claim 18 wherein said supply means additionally includes an auxiliary cryogen supply vessel and conduit means for ducting cryogen from said auxiliary vessel to said reservoir.

20. The apparatus of claim 19 wherein said supporting structure defines an inlet opening in communication with said reservoir for supplying cryogen to said reservoir, and said conduit means is extensible through said inlet opening to transfer cryogen from said auxiliary vessel to said reservoir.

21. The apparatus of claim 18 wherein said vessel comprises:
   a. a container defining a closed chamber for receiving and retaining liquid cryogen therein;
   b. a dispensing tube extending into the lower region of said chamber, said dispensing tube having an inlet opening positioned to be submerged in liquid cryogen when liquid cryogen is present in said chamber and an outlet opening located outside said chamber;
   c. a vent tube extending into the upper region of said chamber, said vent tube having an inlet opening positioned to communicate with gases above any liquid cryogen in said chamber and an outlet opening outside said chamber;
   d. said vent tube being operative when open to vent to the atmosphere such gases as boil away from liquid cryogen in said chamber;
   e. said dispensing tube being operative to duct liquid cryogen out of said container when said vent tube has been closed thereby causing gas pressure to build up within said chamber.

22. A cryogenic apparatus comprising:
   a. a probe structure defining a vacuum evacuable cryogen chamber with deformable wall portions positionable in engagement with surfaces to be cooled and including a porous mass of material positioned in contact with said deformable wall portions and defining an array of random cryogen flow paths for ducting liquid cryogen into contact with said thin wall portions;
   b. a cryogen supply tube adapted for connection to a source of liquid cryogen and extending into said chamber for delivering cryogen to said porous mass; and
   c. connection means adapted to communicate said chamber with a vacuum source.

23. The apparatus of claim 22 wherein said connection means includes a liquid trap including a pressure relief means, for preventing the flow of liquid cryogen to said vacuum source.

24. A method of cooling selected surface areas comprising the steps of:
   a. providing a deformable mass of porous material sheathed with a liquid-cryogen-impervious membrane capable of confining liquid cryogen within said mass, said mass being deformable to provide outer surface portions which substantially conform to the contour of a surface to be treated and being capable following deformation of substantially retaining its deformed configuration;
   b. conforming the membrane covered mass to a configuration which corresponds to the size and shape of a surface to be treated;
   c. pressing the preshaped membrane covered mass into firm engagement with a surface to be treated; and,
   d. introducing a controlled supply of liquid cryogen into said mass whereby the liquid cryogen flows through said mass into contact with said membrane and heat is transferred from a surface to be treated through said membrane to said liquid cryogen.

25. The method of claim 24 additionally including the step of providing insulation means between portions of said membrane and said porous material.

26. The method of claim 25 wherein portions of said insulation means are inflatable, and the method includes the additional step of inflating said inflatable portions prior to introducing liquid cryogen into said mass.

27. The method of claim 24 wherein the step of introducing a controlled supply of liquid cryogen into said mass includes the steps of:
   a. isolating a quantity of liquid cryogen in a container having a closed chamber;
   b. providing a dispensing tube with an inlet opening submerged in the liquid cryogen and an outlet opening outside said container;
   c. positioning said dispensing tube outlet opening near said mass; and
   d. selectively controlling the venting of gases boiling off the liquid cryogen to effect a build-up of sufficient gas pressure to force liquid cryogen out of the container through said dispensing tube and into said mass.

28. The method of claim 27 additionally including the step of providing said container with a vent tube for venting gases boiling off the liquid cryogen, and the step of controlling venting is carried out by selectively opening and closing said vent tube.

29. A cryoprobe comprising a tubular supporting structure, and a deformable, moldable tip connected to the tubular supporting structure, said tip including a portion secured to the tubular structure near one end and a remaining portion extending axially outwardly from that end, said remaining portion being moldable independent of the supporting structure to conform an outer surface portion to a shape that substantially conforms to the shape of a surface to be treated, the tip being capable of substantially retaining its deformed configuration for use.

30. The cryoprobe of claim 29 wherein the moldable tip includes a deformable moldable porous mass whose remaining portion is sheathed by a resilient cryogen-impervious membrane attached to said supporting structure.

31. A method of cooling a selected surface area, comprising the steps of:
   a. molding a portion of a deformable, moldable tip connected to a tubular cryoprobe support to a shape in which an outer surface of the molded portion of the tip substantially conforms to the shape of a surface to be treated, the molded portion of the tip being moldable independent of the tubular support;
   b. pressing the outer surface portion of the molded portion of the tip into firm engagement with a surface area to be treated; and,
   c. introducing a cryogen through the support and into the tip to cool the surface area engaging the tip.

32. The method of claim 31 wherein the step of introducing cryogen into the tip is effected by transmitting cryogen through a porous deformable mass which forms at least a part of the tip.

* * * * *

UNITED STATES PATENT AND TRADEMARK OFFICE
CERTIFICATE OF CORRECTION

PATENT NO. : 4,022,215

DATED : June 10, 1977

INVENTOR(S) : Jerrel W. Benson

It is certified that error appears in the above-identified patent and that said Letters Patent are hereby corrected as shown below:

Column 1, line 27, delete "liguid" and insert -- liquid --.

Column 1, Line 62, after "technique" insert - - unsuitable - -

Column 2, Line 47, delete "system" and substitute - - systems - -

Column 2, Line 48, delete "regualting" and substitute - - regulating - -

Column 3, Line 16, delete "deforamble" and substitute - - deformable - -

Column 4, line 7, after "membrane" insert - - must have sufficient structural integrity to effectively isolate - -

Column 7, line 28, delete "cryogenn" and substitute - - cryogen - -

Signed and Sealed this

Twenty-second Day of November 197:

[SEAL]

Attest:

RUTH C. MASON
Attesting Officer

LUTRELLE F. PARKER
Acting Commissioner of Patents and Trademark